(12) United States Patent
Anderson et al.

(10) Patent No.: US 11,672,541 B2
(45) Date of Patent: Jun. 13, 2023

(54) MEDICAL DEVICE WITH OCCLUSIVE MEMBER

(71) Applicant: BOSTON SCIENTIFIC SCIMED, INC., Maple Grove, MN (US)

(72) Inventors: James M. Anderson, Corcoran, MN (US); David John Onushko, Maple Grove, MN (US); Joshua Mark Inouye, Maple Grove, MN (US); Steven R. Larsen, Lino Lakes, MN (US); Daniel H. VanCamp, Elk River, MN (US); John M. Edgell, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 207 days.

(21) Appl. No.: 16/434,661

(22) Filed: Jun. 7, 2019

(65) Prior Publication Data
US 2019/0374229 A1    Dec. 12, 2019

Related U.S. Application Data

(60) Provisional application No. 62/682,201, filed on Jun. 8, 2018.

(51) Int. Cl.
*A61B 17/12* (2006.01)
*A61B 17/00* (2006.01)

(52) U.S. Cl.
CPC .. *A61B 17/12122* (2013.01); *A61B 17/12172* (2013.01); *A61B 2017/00632* (2013.01);
(Continued)

(58) Field of Classification Search
CPC ........ A61B 17/12172; A61B 17/12168; A61B 17/12177; A61B 2017/12054;
(Continued)

(56) References Cited

U.S. PATENT DOCUMENTS

| | | |
|---|---|---|
| 1,782,830 A | 6/1876 | French |
| 1,967,318 A | 10/1931 | Monahan |

(Continued)

FOREIGN PATENT DOCUMENTS

| | | |
|---|---|---|
| CN | 106859722 A | 6/2017 |
| WO | 9313712 A1 | 7/1993 |

(Continued)

OTHER PUBLICATIONS

Invitation to Pay Additional Fees dated Aug. 19, 2019 for International Application No. PCT/US2019/036063.
(Continued)

*Primary Examiner* — Sarah A Simpson
*Assistant Examiner* — Raihan R Khandker
(74) *Attorney, Agent, or Firm* — Seager, Tufte & Wickhem LLP

(57) ABSTRACT

An example occlusive implant is disclosed. The example occlusive implant includes an expandable framework configured to shift between a first configuration and a second expanded configuration, an occlusive member disposed along at least a portion of an outer surface of the expandable framework and a resilient member coupled to the occlusive member. Further, the resilient member is configured to keep the occlusive member taut against an outer surface of the expandable member in both the first configuration and the second configuration.

16 Claims, 15 Drawing Sheets

(52) U.S. Cl.
CPC .............. *A61B 2017/00862* (2013.01); *A61B 2017/12054* (2013.01)

(58) Field of Classification Search
CPC .... A61B 2017/00862; A61B 17/12122; A61B 2017/00632; A61B 17/12109–12118
See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |

(56) References Cited

U.S. PATENT DOCUMENTS

| | | |
|---|---|---|
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,096,053 A | 8/2000 | Bates |
| 6,110,243 A | 8/2000 | Wnenchak et al. |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,251,122 B1 | 6/2001 | Tsukernik |
| 6,258,115 B1 | 7/2001 | Dubrul |
| 6,270,490 B1 | 8/2001 | Hahnen |
| 6,277,138 B1 | 8/2001 | Levinson et al. |
| 6,290,674 B1 | 9/2001 | Roue et al. |
| 6,319,251 B1 | 11/2001 | Tu et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,364,895 B1 | 4/2002 | Greenhalgh |
| 6,368,338 B1 | 4/2002 | Knya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,511,496 B1 | 1/2003 | Huter et al. |
| 6,517,573 B1 | 2/2003 | Pollock et al. |
| 6,547,760 B1 | 4/2003 | Samson et al. |
| 6,551,303 B1 | 4/2003 | Van Tassel et al. |
| 6,551,344 B2 | 4/2003 | Thill |
| 6,558,405 B1 | 5/2003 | McInnes |
| 6,562,058 B2 | 5/2003 | Seguin et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,730,108 B2 | 5/2004 | Van Tassel et al. |
| 6,837,901 B2 | 1/2005 | Rabkin et al. |
| 6,855,153 B2 | 2/2005 | Saadat |
| 6,949,113 B2 | 9/2005 | Van Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | van der Burg et al. |
| 8,062,282 B2 | 11/2011 | Kolb |
| 8,491,623 B2 | 7/2013 | Vogel et al. |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0082638 A1 | 6/2002 | Porter et al. |
| 2002/0138094 A1 | 9/2002 | Borillo et al. |
| 2002/0138097 A1 | 9/2002 | Ostrovsky et al. |
| 2003/0023266 A1 | 1/2003 | Borillo et al. |
| 2003/0057156 A1 | 3/2003 | Peterson et al. |
| 2003/0181942 A1 | 9/2003 | Sutton et al. |
| 2003/0220667 A1 | 11/2003 | van der Burg et al. |
| 2004/0098031 A1 | 5/2004 | van der Burg et al. |
| 2004/0215230 A1 | 10/2004 | Frazier et al. |
| 2005/0004652 A1 | 1/2005 | van der Burg et al. |
| 2005/0113861 A1 | 5/2005 | Corcoran et al. |
| 2005/0203568 A1 | 9/2005 | Burg et al. |
| 2014/0018841 A1 | 1/2014 | Peiffer et al. |
| 2014/0039536 A1 | 2/2014 | Cully et al. |
| 2014/0100596 A1 | 4/2014 | Rudman et al. |
| 2014/0188157 A1* | 7/2014 | Clark ............... A61B 17/12122 606/200 |
| 2014/0336612 A1 | 11/2014 | Frydlewski et al. |
| 2014/0364941 A1* | 12/2014 | Edmiston ......... A61B 17/12022 623/2.11 |
| 2016/0106437 A1 | 4/2016 | Van Der Burg et al. |
| 2016/0287259 A1 | 10/2016 | Hanson et al. |
| 2018/0042719 A1* | 2/2018 | Chambers ............. A61F 2/2418 |
| 2019/0223883 A1 | 7/2019 | Anderson et al. |
| 2020/0138446 A1* | 5/2020 | Jockenhoevel .... A61B 17/1215 |

FOREIGN PATENT DOCUMENTS

| | | |
|---|---|---|
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |
| WO | 03032818 A2 | 4/2003 |
| WO | 2015164836 A1 | 10/2015 |
| WO | 2016183495 A2 | 11/2016 |
| WO | 2018017935 A1 | 1/2018 |
| WO | 2018187732 A1 | 10/2018 |

OTHER PUBLICATIONS

PCT Search Report from co-pending Application PCT/US02/33808 dated May 20, 2003.
PCT Search Report from PCT/US99/26325 dated Feb. 15, 2000.

(56) References Cited

OTHER PUBLICATIONS

Cragg et al; "Nonsurgical Placement of Arterial Endoprosthesis: A New Technique Using Nitinol Wire," Radiology vol. 147, No. 1 pp. 261-263, Apr. 1983.
Cragg et al; "A New Percutaneous Vena Cava Filter", ALJ, 141: 601-604, Sep. 1983.
Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruttenberg, Nonsurgical Therapy of Cardiac Disorders, Pediatric Consult, vol. 5, No. 2, pages not numbered, 1986.
Rashkind et al; Nonsurgical Closure of Patent Ductus Arteriosus: Clinical Application of the Rashkind PDA Occluder System, Circulation 75, No. 3, 583-592-1987.
Lock et al.; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Invite to Pay Additional Fees dated Feb. 22, 2019 for International Application No. PCT/US2018/066163.
International Search Report and Written Opinion dated Sep. 9, 2019 for International Application No. PCT/US2019/033698.

* cited by examiner

MEDICAL DEVICE WITH OCCLUSIVE MEMBER

CROSS-REFERENCE TO RELATED APPLICATIONS

This application claims the benefit of priority under 35 U.S.C. § 119 to U.S. Provisional Application Ser. No. 62/682,201, filed Jun. 8, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

An example occlusive implant include an expandable framework configured to shift between a first configuration and a second expanded configuration, an occlusive member disposed along at least a portion of an outer surface of the expandable framework and a resilient member coupled to the occlusive member. Further, the resilient member is configured to keep the occlusive member taut against an outer surface of the expandable member in both the first configuration and the second configuration.

In addition or alternatively, wherein the resilient member includes a spring having a first end attached to the occlusive member and a second end coupled to the expandable frame.

In addition or alternatively, wherein the resilient member includes an elastic band having a first end attached to the occlusive member and a second end coupled to the expandable frame.

In addition or alternatively, wherein further comprising a first resilient member including a spring and a second resilient member including an elastic band, wherein each of the spring and the elastic band has a first end attached to the occlusive member and a second end coupled to the expandable frame.

In addition or alternatively, wherein the resilient member includes one or more elastic fibers integrated with the occlusive member, and wherein the one or more elastic fibers are deigned to elongate and contract as the expandable member shifts between the first configuration and the second expanded configuration.

In addition or alternatively, wherein the occlusive member includes one or more inelastic fibers and wherein the one or more elastic fibers are interwoven with the one or more inelastic fibers.

In addition or alternatively, further comprising a plurality of rigid members disposed along the occlusive member, wherein each of the plurality of rigid members include an aperture designed to permit fluid to flow therethrough.

In addition or alternatively, wherein the occlusive member includes a mesh structure, and wherein the resilient member includes one or more elastic members interconnected to form an elastic matrix, and wherein the mesh structure is coupled to the elastic matrix.

In addition or alternatively, wherein the expandable matrix includes a plurality of interstices spaced throughout the matrix, and wherein the mesh structure is disposed within the plurality of interstices.

In addition or alternatively, further comprising a hub member disposed adjacent the occlusive member, and wherein the resilient member includes a coil member disposed around the hub member, and wherein the coil member is designed to tighten the occlusive member as the expandable member shifts between the first configuration and the second expanded configuration.

In addition or alternatively, further comprising a hub member disposed adjacent the occlusive member, and wherein the resilient member includes a ratcheting member disposed around the hub member, and wherein the ratcheting member is designed to rotate and tighten the occlusive member as the expandable member shifts between the first configuration and the second expanded configuration.

In addition or alternatively, further comprising a core wire coupled to the ratcheting member, and wherein the core wire is designed to rotate the ratcheting member.

Another occlusive implant includes:
an expandable framework configured to shift between a first configuration and a second expanded configuration;
an occlusive member disposed along at least a portion of an outer surface of the expandable framework; and
a tightening member coupled to the expandable framework, the occlusive member or both the expandable framework and the occlusive member;
wherein rotation of the tightening member is configured to keep the occlusive member taut against an outer surface of the expandable member in both the first configuration and the second configuration.

In addition or alternatively, further comprising a hub member coupled to the expandable framework, and wherein the tightening member includes a coil member disposed along the hub member, and wherein rotation of the coil member is designed to keep the occlusive member taut against the outer surface of the expandable member in both the first configuration and the second configuration.

In addition or alternatively, wherein the coil member is wound around an outer surface of the hub member.

In addition or alternatively, further comprising a hub member coupled to the expandable framework, and wherein the tightening member includes a ratcheting member disposed adjacent to the hub member, and wherein rotation of the ratcheting member is designed to keep the occlusive member taut against the outer surface of the expandable member in both the first configuration and the second configuration.

In addition or alternatively, further comprising a core wire coupled to the ratcheting member, and wherein rotating the core wire in a first direction is designed to rotate the ratcheting member.

In addition or alternatively, wherein the ratcheting member is designed to rotate in a first direction, and wherein the ratcheting member is prevented from rotating in a second direction opposite the first direction, and wherein the occlusive member is tightened when the ratcheting member is rotated in the first direction.

In addition or alternatively, wherein rotation of the core wire in the second direction is designed to separate the core wire from the ratcheting member while the ratcheting member keeps the occlusive member taut against the outer surface of the expandable member.

A method for occluding a left atrial appendage includes:
advancing an occlusive implant to the left atrial appendage, the occlusive implant including:
an expandable framework configured to shift between a first configuration and a second expanded configuration;
an occlusive member disposed along at least a portion of an outer surface of the expandable framework;
a resilient member coupled to the occlusive member;
expanding the expandable framework within the left atrial appendage, wherein during expanding the expandable framework within the left atrial appendage the resilient member keeps the occlusive member taut against an outer surface of the expandable member.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
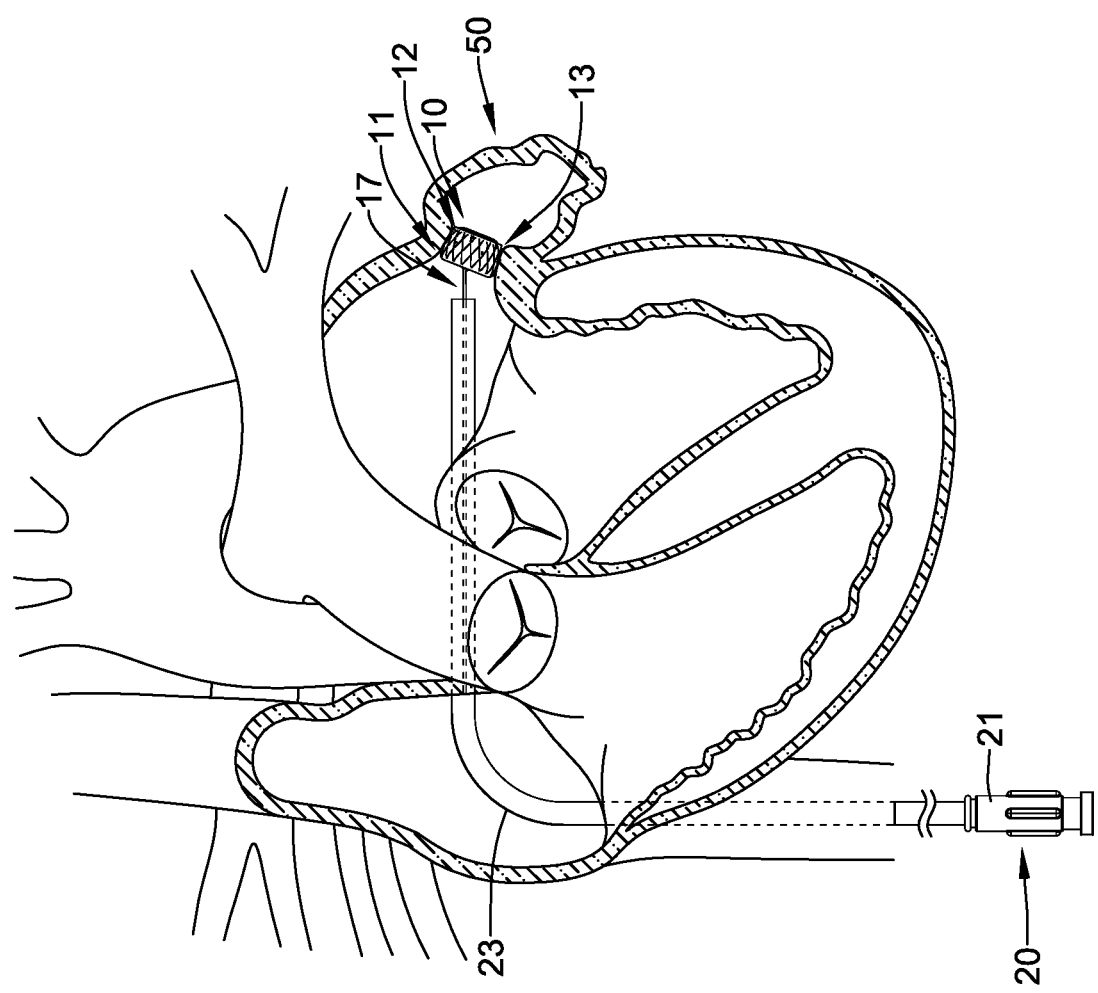
FIG. 1 shows an example occlusive implant positioned in the heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thromboembolic material entering the blood stream from the left atrial appendage. Example medical devices and/or occlusive implants that close off the left atrial appendage are disclosed herein.

FIG. 1 illustrates an occlusive implant 10 which has been inserted and advanced through a body lumen via an occlusive implant delivery system 20. FIG. 1 further illustrates the occlusive implant 10 being delivered and positioned within the left atrial appendage 50. As will be described in greater detail below, the occlusive implant 10 may include an expandable framework 12 which includes a proximal end region 11 and a distal end region 13 In some instances, an occlusive implant delivery system 20 may include a delivery catheter 23 which is guided toward the left atrium via various chambers and lumens of the heart (e.g., the inferior vena cava, the right atrium, etc.) to a position adjacent the left atrial appendage 50.

The delivery catheter 23 may include a manifold 21. The manifold 21 may be manipulated by a clinician to direct the distal end region of the delivery catheter 23 to a position adjacent the left atrial appendage 50. In some embodiments, an occlusive implant delivery system may include a core wire 17. Further, a proximal end region 11 of the expandable framework 12 may be configured to releasably attach, join, couple, engage, or otherwise connect to the distal end of the core wire 17. In some embodiments, the proximal end region 11 of the expandable framework 12 may include a threaded insert coupled thereto. In some embodiments, the threaded insert may be configured to and/or adapted to couple with, join to, mate with, or otherwise engage a threaded member disposed at the distal end of a core wire 17. Other means of releasably coupling and/or engaging the proximal end region 11 of the expandable framework 12 to the distal end of the core wire 17 are also contemplated.

FIG. 1 further illustrates the occlusive implant 10 positioned adjacent the left atrial appendage 50 via the delivery catheter 23 (described above). It can be appreciated that in some examples, the implant 10 may be configured to shift between a collapsed configuration and an expanded configuration. For example, in some instances, the occlusive implant 10 may be in a collapsed configuration during delivery via occlusion implant delivery system, whereby the occlusive implant 10 expands to an expanded configuration once deployed from the occlusion implant delivery system.

In some instances, it may be desirable to design the occlusive implant 10 described herein to include features which allow it to accommodate patient-to-patient variability in the shape of the left atrial appendage. In other words, it may be desirable to design the occlusive implant 10 such that a clinician may utilize the same device irrespective of the particular anatomy presented by a particular patient. For example, it is known that the diameter of the opening (e.g., orifice) of the left atrial appendage may vary widely among individuals. In particular, the diameter of the opening to the left atrial appendage may be narrower in certain individuals as compared to others. Therefore, it may be desirable to design the occlusive implant 10 such that it can change its shape to fit different orifice diameters of the left atrial appendage without sacrificing its effectiveness in sealing the left atrial appendage. In particular, it may be desirable to design the occlusive implant 10 such that it can expand or collapse without substantially changing the distance in which it extends into the left atrial appendage and without substantially changing the radial force in which it exerts upon the surrounding tissue. For example, the expandable framework 12 illustrated in FIG. 1 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue and/or lateral wall of the left atrial appendage 50.

Further, it can be appreciated that the structural elements of the expandable framework 12 may be tailored to increase the flexibility of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 to include various features, components and/or configurations which improve the sealing capabilities of the occlusive implant 10 within the left atrial appendage 50.

For example, FIG. 1 illustrates that the distal end region 13 of the expandable framework 12 may extend farther into the left atrial appendage 50 as compared to the proximal end region 11 of the expandable framework 12. It can be appreciated that as the expandable framework is advanced into the left atrial appendage 50, the distal end region 13 may engage with tissue defining the left atrial appendage 50. In other words, the distal end region 13 may be considered the "leading" region of the expandable framework 12 as it enters into the left atrial appendage 50. Therefore, it can further be appreciated that it may be desirable to design the distal end region 13 of the expandable framework to the include features which provide an atraumatic engagement with the heart tissue defining the left atrial appendage 50. Examples of occlusive implants including features designed to provide atraumatic engagement with the heart tissue are described below.

Figure 2:
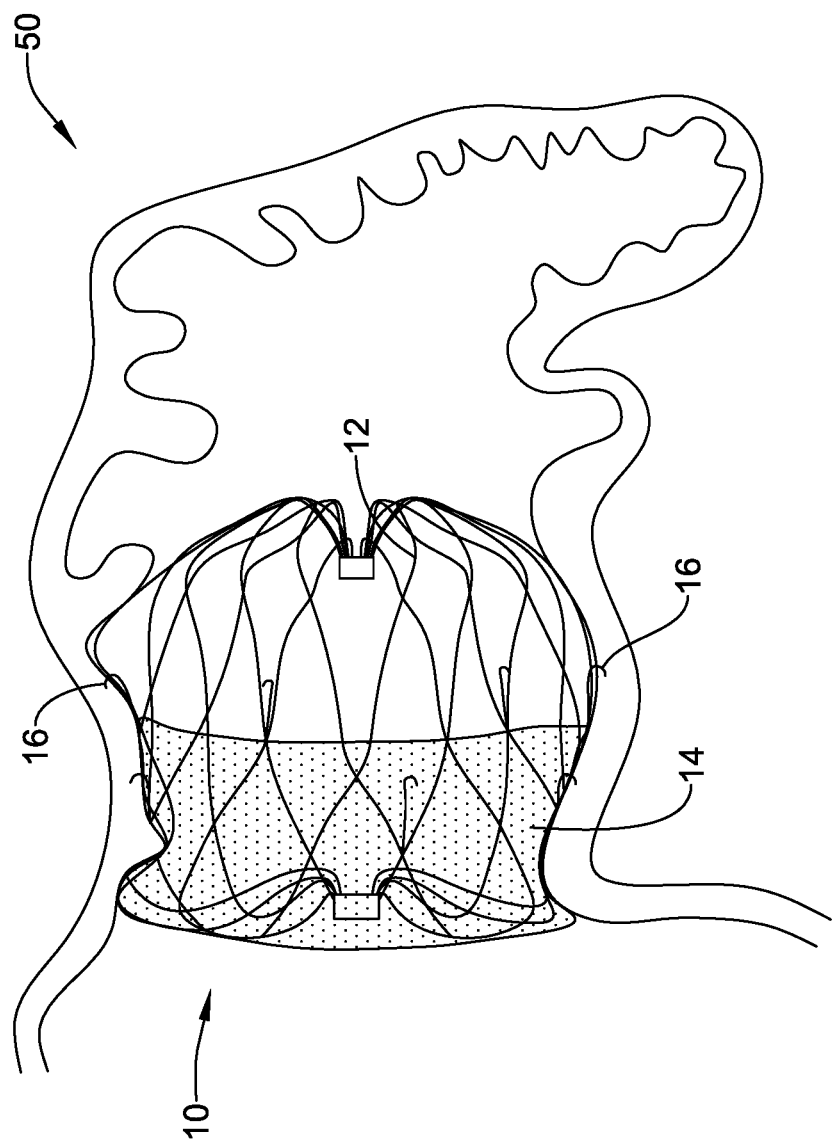
FIG. 2 shows an example occlusive implant positioned in the left atrial appendage.

FIG. 2 illustrates a left atrial appendage occlusive implant 10 positioned adjacent the left atrial appendage 50 via the delivery catheter 23 (described above with respect to FIG. 1). As discussed above, in some examples, the implant 10 may be configured to shift between a collapsed configuration and an expanded configuration. For example, in some instances, the occlusive implant 10 may be in a collapsed configuration during delivery via the occlusion implant delivery system, whereby the occlusive implant 10 expands to an expanded configuration once deployed from the occlusion implant delivery system.

Additionally, FIG. 2 illustrates that the expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue and/or lateral wall of the left atrial appendage 50. Additionally, FIG. 2 illustrates that the expandable framework 12 may be held fixed adjacent to the left atrial appendage 50 by one or more anchoring members 16. Further, as will be discussed in greater detail below, the occlusive implant 10 may also include an occlusive member 14 disposed on, disposed over, disposed about, or covering at least a portion of the expandable framework 12.

Figure 3:
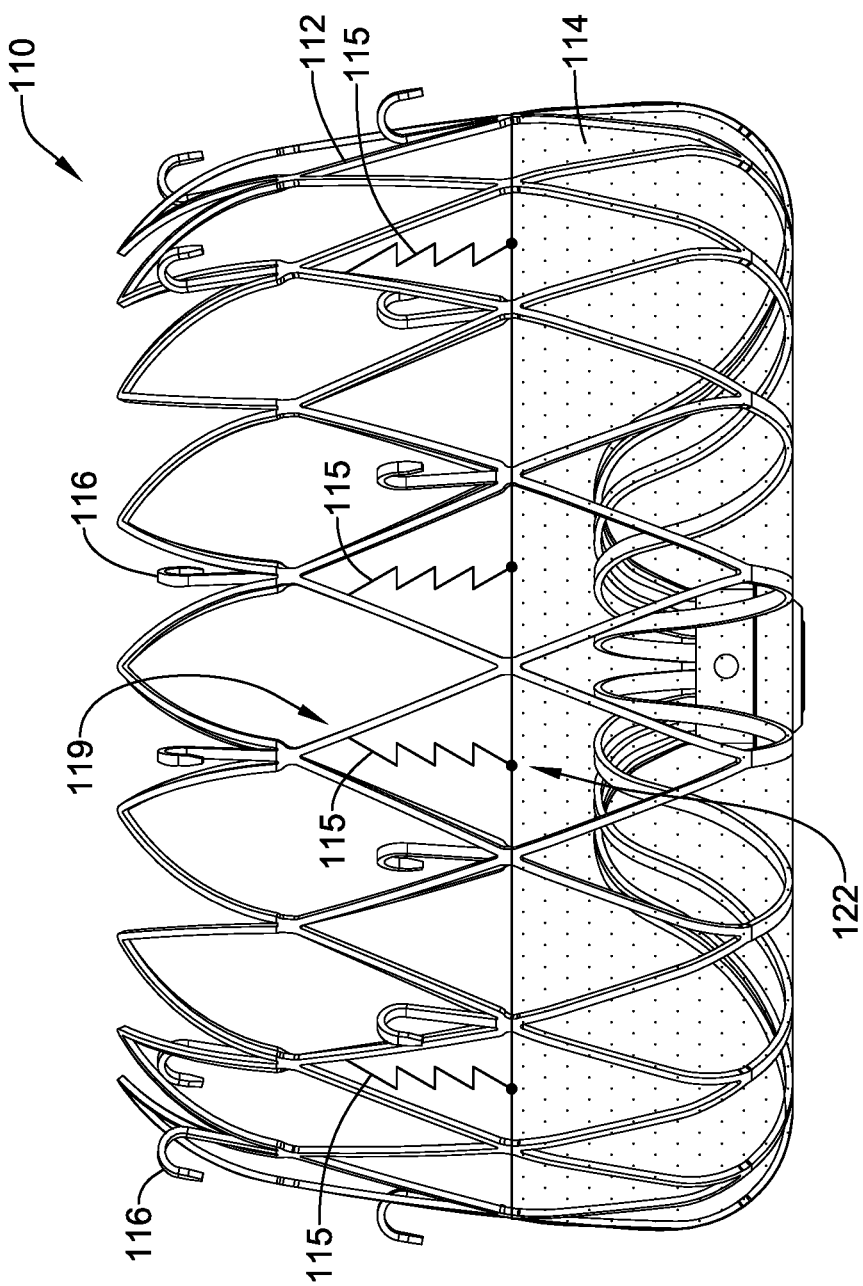
FIG. 3 illustrates an example occlusive implant.

FIG. 3 illustrates an example occlusive implant 110. The occlusive implant 110 may be similar in form and function to other implants described herein (e.g., the implant 10). The implant 110 may include an expandable framework 112. The occlusive implant 110 may also include an occlusive member 114 disposed on, disposed over, disposed about, or covering at least a portion of the expandable framework 112. In some embodiments, the occlusive member 114 may be disposed on, disposed over, disposed about or cover at least a portion of an exterior (or outwardly-facing) surface of the expandable framework 112. FIG. 3 further illustrates that the occlusive member 114 may extend only partially along the longitudinal extent of the expandable framework 112. However, this is not intended to be limiting. Rather, the occlusive member 114 may extend along the longitudinal extent of the expandable framework to any degree (e.g., the full longitudinal extend of the expandable framework 112).

In some embodiments, the occlusive member 114 may be permeable or impermeable to blood and/or other fluids, such as water. In some embodiments, the occlusive member 114 may include a woven, braided and/or knitted material, a fiber, a sheet-like material, a fabric, a polymeric membrane, a metallic or polymeric mesh, a porous filter-like material, or other suitable construction. In some embodiments, the occlusive member 114 may prevent thrombi (e.g., blood clots, etc.) from passing through the occlusive member 114 and out of the left atrial appendage into the blood stream. In some embodiments, the occlusive member 114 may promote endothelization after implantation, thereby effectively removing the left atrial appendage from the patient's circulatory system. Some suitable, but non-limiting, examples of materials for the occlusive member 114 are discussed below.

FIG. 3 further illustrates that the expandable framework 112 may include a plurality of anchor members 116 disposed about a periphery of the expandable framework 112. The plurality of anchor members 116 may extend radially outward from the expandable framework 112. In some embodiments, at least some of the plurality of anchor members 116 may each have and/or include a body portion and a tip portion projecting circumferentially therefrom, as shown in FIG. 3. Some suitable, but non-limiting, examples of materials for the expandable framework 112 and/or the plurality of anchor members 116 are discussed below.

In some examples, the expandable framework 112 and the plurality of anchor members 116 may be integrally formed and/or cut from a unitary member. In some embodiments, the expandable framework 112 and the plurality of anchor members 116 may be integrally formed and/or cut from a unitary tubular member and subsequently formed and/or heat set to a desired shape in the expanded configuration. In some embodiments, the expandable framework 112 and the plurality of anchor members 116 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 112 include laser cutting, machining, punching, stamping, electro discharge machining (EDM), chemical dissolution, etc. Other means and/or methods are also contemplated.

As illustrated in FIG. 3, the plurality of anchor members 116 disposed along the expandable framework 112 may include two rows of anchor members 116. However, this is not intended to be limiting. Rather, the expandable framework 112 may include a single row of anchor members 116. In other examples, the expandable framework 112 may include more than two rows of anchor members 116. For example, in some instances the expandable framework 112 may include 1, 2, 3, 4 or more rows of anchor members 116.

As discussed above, in some instances it may be desirable to design the medical device implants disclosed herein to accommodate a variety of different patient populations (e.g., to accommodate the different shapes of left atrial appendages across different patients). For example, the medical device 110 may be designed such that it may expand and/or contract depending upon the particular diameter of a left atrial appendage in which it is being positioned. Further, it can be appreciated that an occlusive member disposed on, disposed over, disposed about or covering at least a portion of an outer (or outwardly-facing) surface of the expandable framework 112 may also be designed to expand and/or contract coincident with the expansion and/or contract of the expandable framework 112.

It can be appreciated that a variety of different structures may be incorporated within the expandable framework 112 and/or the occlusive member 114 which are designed to permit the occlusive member 114 to remain disposed along the outer surface of the expandable framework 112 as the expandable framework 112 shifts between an unexpanded and an expanded configuration. In other words, a variety of different structures may be incorporated within the expandable framework 112 and/or the occlusive member 114 which are designed to maintain the occlusive member 114 under tension (e.g., substantially taut) along the outer surface of the expandable framework 112. Keeping the occlusive member 114 taut along the outer surface of the expandable framework 112 may prevent the occlusive member 114 from forming wrinkles therein as the expandable framework shift between an unexpanded configuration and an expanded configuration. It may be desirable to reduce wrinkles in the occlusive member 114 to reduce the likelihood that particulate (e.g., thrombus) may be trapped therein.

Additionally, FIG. 3 illustrates that the medical device 110 may include one or more spring (e.g., tether) members 115. Each of the spring members 115 may include a first end coupled to the occlusive member 114 at a connection point 122 and a second end (opposite the first end) which is coupled to a portion of the expandable framework 112. Further, each of the spring members 115 may include a coiled portion, helical portion, twisted region, zig-zag portion, looped portion, or combinations thereof. It can be appreciated that the spring members 115 may be able to be compressed or stretched from a relaxed position. It can be further appreciated that each of the spring members 115 may be designed such that they pull the first end of the spring members 115 toward the second end of the spring members 115, thereby maintaining tension on the occlusive member 114. The tension placed on the occlusive member 114 via each of the spring members 115 may keep the occlusive member 114 taut against the outer surface of the expandable framework 112. Further, it can be appreciated that the ability of the spring members 115 to expand and/or contract while maintaining a tension along the occlusive member 114 may keep the occlusive member 114 taut against the outer surface of the expandable framework 112 as the size (e.g., diameter) of the expandable framework 112 changes (e.g., via expansion or contraction). While FIG. 3 shows the medical device 110 including four spring members 115, more or less than four spring members 115 are contemplated. For example, the medical device 110 may include 1, 2, 3, 4, 5, 6, 7, 8, 9, 10 or more spring members 115.

Figure 4:
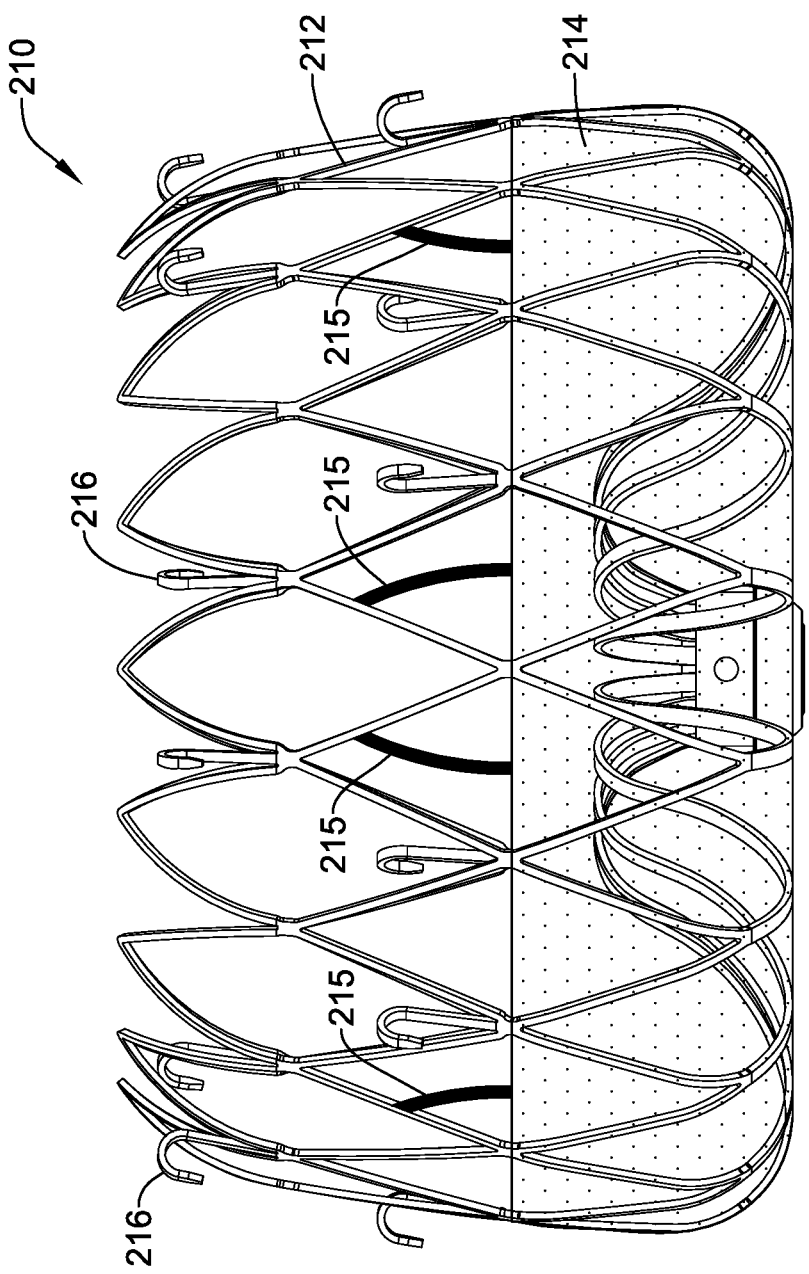
FIG. 4 illustrates another example occlusive implant.

FIG. 4 illustrates another example medical device 210. The example medical device 210 may be similar in form and function to other medical devices described above. For example, the medical device 210 may include an expandable framework 212. The expandable framework 212 may be configured to shift between an unexpanded configuration and an expanded configuration. Additionally, the medical device 210 may include one or more anchor members 216 coupled to the expandable framework 212. Similar to medical device 10 described above, the medical device 210 may include an occlusive member 214 disposed along the exterior surface of the expandable framework 212.

Additionally, FIG. 4 illustrates that the medical device 210 may include one or more elastic bands 215. Each of the elastic bands 215 may include a first end coupled to the occlusive member 214 and a second end (opposite the first end) which is coupled to a portion of the expandable framework 112. Further, each of the elastic bands 215 may include a straight portion, a curved region, or combinations thereof. It can be appreciated that the elastic bands 215 may be compressed or stretched from a relaxed position. It can be further appreciated that each of the elastic bands 215 may be designed such that they contract and pull on the occlusive member 214, thereby maintaining tension on the occlusive member 214. The tension placed on the occlusive member 214 via each of the elastic bands 215 may keep the occlusive member 214 taut against the outer surface of the expandable member 212. Further, it can be appreciated that the ability of the elastic bands 215 to expand and/or contract while maintaining a tension along the occlusive member 214 may keep the occlusive member 214 taut against the outer surface of the expandable member 212 as the size (e.g., diameter) of the expandable member 212 changes (e.g., via expansion or contraction). While FIG. 4 shows the medical device 210 including four elastic bands 215, more or less than four elastic bands 215 are contemplated. For example, the medical device 110 may include 1, 2, 3, 4, 5, 6, 7, 8, 9, 10 or more elastic bands 215.

Figure 5:
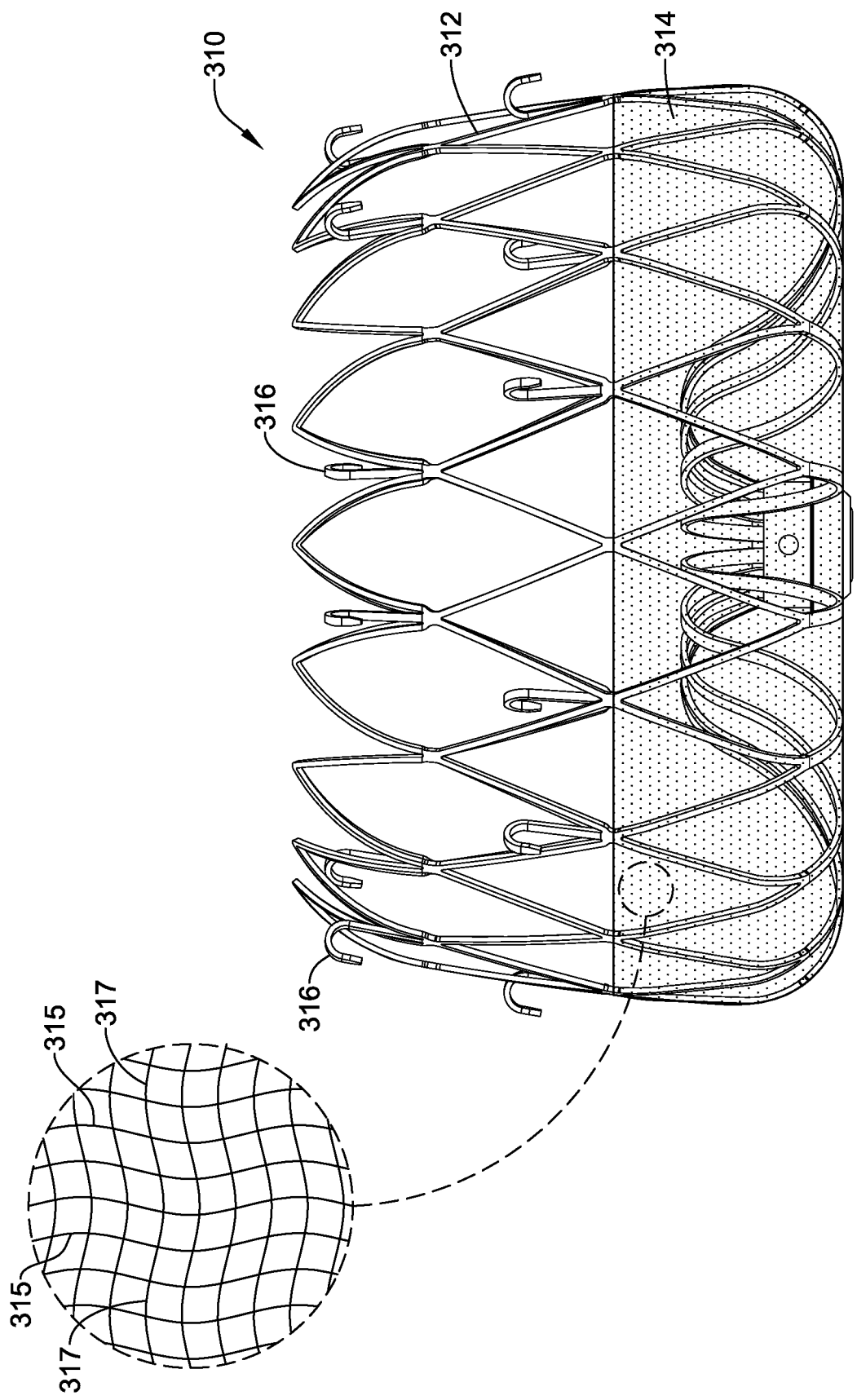
FIG. 5 illustrates another example occlusive implant.

FIG. 5 illustrates another example medical device 310. The example medical device 310 may be similar in form and function to other medical devices described above. For example, the medical device 310 may include an expandable framework 312. The expandable framework 312 may be configured to shift between an unexpanded configuration and an expanded configuration. Additionally, the medical device 310 may include one or more anchor members 316 coupled to the expandable framework 312. Similar to medical device 10 described above, the medical device 310 may include an occlusive member 314 disposed along the exterior surface of the expandable framework 312.

Additionally, the detailed view of FIG. 5 illustrates that, in some examples, it may be beneficial to design the occlusive member 314 to include a woven (e.g., braided, knitted, etc.) mesh. In some examples, the woven mesh may include a combination of inelastic and/or elastic materials. For example, the detailed view of FIG. 5 illustrates that the mesh may include one or more inelastic fibers 315 interlaced (e.g., interwoven) with one or more elastic fibers 317. In other words, the inelastic fibers 315 may alternative with the elastic fibers 317 in variety of configurations. For example, in some examples, an equal number of the inelastic fibers 315 may be interlaced with the elastic fibers 317. However, in other examples, a greater number of the inelastic fibers 315 may be interlaced with the elastic fibers 317. Conversely, in some examples, a greater number of the elastic fibers 317 may be interlaced with the inelastic fibers 315.

It can be appreciated that the elastic fibers 317 may be compressed or stretched from a relaxed position. It can be further appreciated that the elastic fibers 317 may be designed such that they keep the occlusive member 314 taut against the outer surface of the expandable framework 312. Further, it can be appreciated that the ability of the elastic fibers 317 to expand and/or contract while maintaining a tension along the occlusive member 314 may keep the occlusive member 314 taut against the outer surface of the expandable framework 312 as the size of the framework member 312 changes (e.g., via expansion or contraction).

Figure 6:
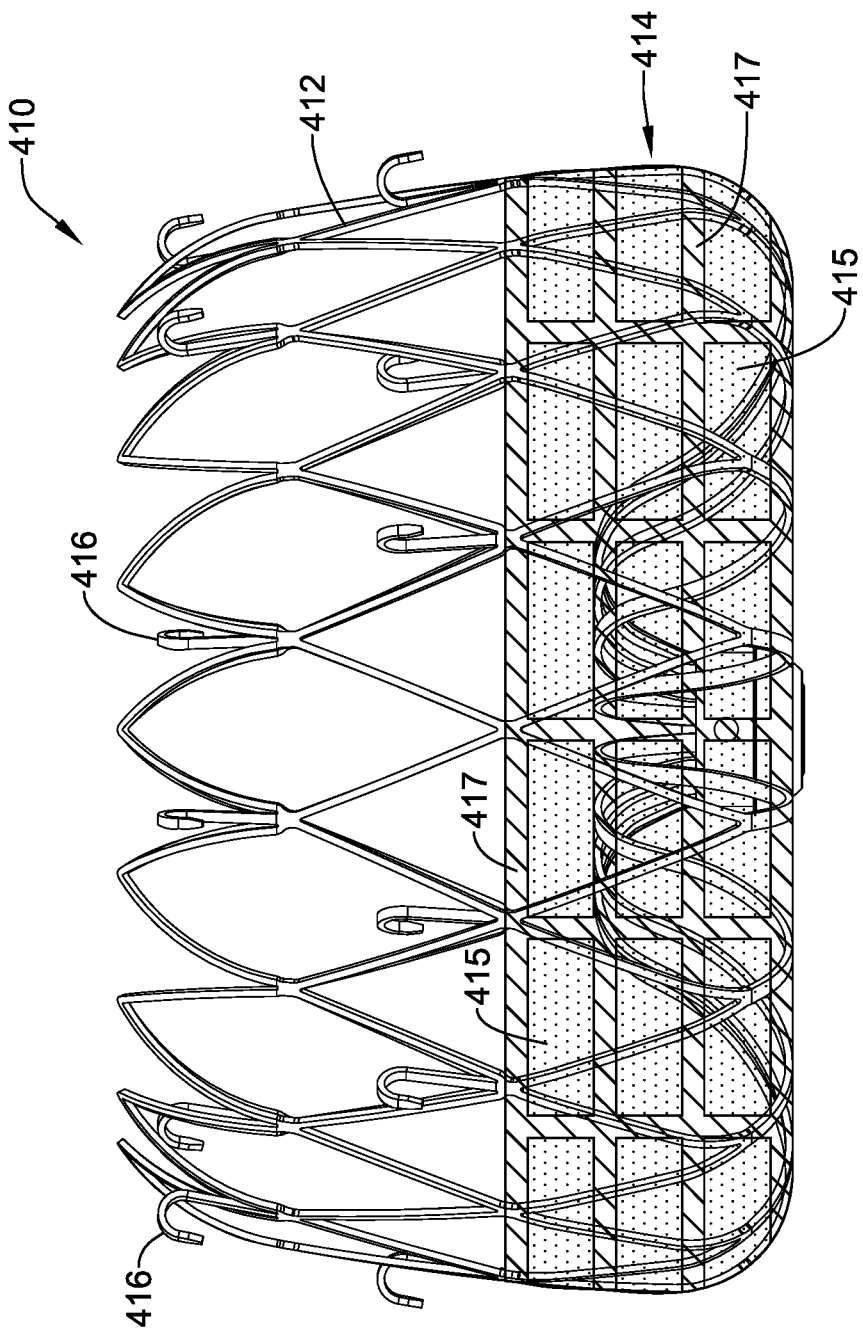
FIG. 6 illustrates another example occlusive implant.

FIG. 6 illustrates another example medical device 410. The example medical device 410 may be similar in form and function to other medical devices described above. For example, the medical device 410 may include an expandable framework 412. The expandable framework 412 may be configured to shift between an unexpanded configuration and an expanded configuration. Additionally, the medical device 410 may include one or more anchor members 416 coupled to the expandable framework 412. Similar to medical device 10 described above, the medical device 410 may include an occlusive member 414 disposed along the exterior surface of the expandable framework 412.

Additionally, FIG. 6 illustrates that in some examples, it may be beneficial to design the occlusive member 414 to include a plurality of elastic elements 417 interconnected with one another to form an elastic matrix. Additionally, the elastic elements 417 may be engaged with one or more mesh portions 415. For example, in some instances, the elastic elements 417 may be integrated within the mesh structure. In some examples, the elastic elements 417 may be interconnected to form interstices (e.g., individual cells) within which the mesh portions 415 are positioned. The mesh portions 415 may be formed from an elastic or inelastic material. In some examples, a combination of inelastic and elastic mesh portions may interspersed within the elastic elements 417.

It can be appreciated that the elastic elements 417 in combination with the woven mesh portions 415 may be compressed or stretched. It can be further appreciated that the elastic elements 417 in combination with the woven mesh portions 415 may be designed such that they keep the occlusive member 414 taut against the outer surface of the expandable framework 412. Further, it can be appreciated that the ability of the elastic elements 417 in combination with the woven mesh portions 415 to expand and/or contract while maintaining a tension along the occlusive member 414 may keep the occlusive member 414 taut against the outer surface of the expandable framework 412 as the size (e.g., diameter) of the expandable framework 412 changes (e.g., via expansion or contraction).

Figure 7:
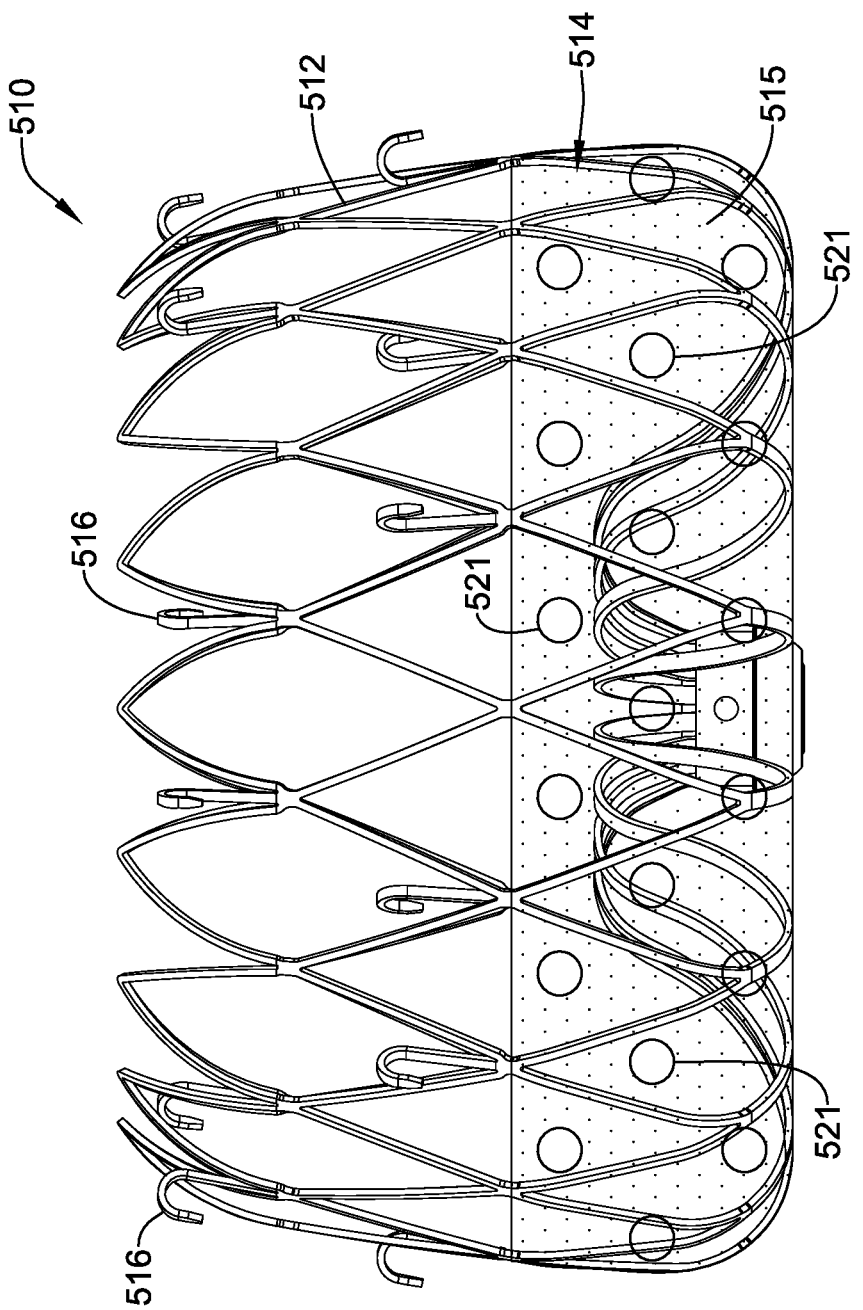
FIG. 7 illustrates another example occlusive implant.

FIG. 7 illustrates an example medical device 510. The example medical device 510 may be similar in form and function to other medical devices described above. For example, the medical device 510 may include an expandable framework 512. The expandable framework 512 may be configured to shift between an unexpanded configuration and an expanded configuration. Additionally, the medical device 510 may include one or more anchor members 516 coupled to the expandable framework 512. Similar to medical device 10 described above, the medical device 510 may include an occlusive member 514 disposed along the exterior surface of the expandable framework 512.

In some instances, it may be beneficial to design the medical device 510 to include one or more apertures 521 disposed along the occlusive member 514. Similar to that described above with respect to the occlusive member 14, the occlusive member 514 may include a mesh structure 515 disposed along the exterior surface of the expandable framework 512. For example, the mesh structure 515 may include elastic fibers woven together to form the mesh structure 515. In some examples, the mesh structure 515 may include inelastic fibers interwoven with the elastic fibers (similar to the mesh structure illustrated and described with respect to the detail view of FIG. 5).

As discussed above, it may be beneficial to include one or more apertures 521 disposed with the mesh structure 515. Each of the apertures 521 may be formed from a rigid material (e.g., polymeric rings), wherein the apertures 521 resist deformation as the occlusive member 514 expands or contracts with the expansion or contraction of the expandable framework 512. However, this is not intended to be limiting. It is contemplated that the apertures 521 may be formed from an elastic and/or semi-rigid material.

In some examples it may be desirable to design the apertures 521 to allow blood to flow therethrough. It can further be appreciated that designing the occlusive member 514 to include a plurality of apertures 521 formed from a rigid material may result in the occlusive member 514 maintaining a consistent "porosity" as the occlusive member 514 expands or contracts with the expansion or contraction of the expandable framework 512. Maintaining a consistent porosity as the occlusive member 514 expands or contracts may be desirable to maintain a consistent volume of blood flowing through the occlusive member 514 independent of the degree to which the expandable framework 512 expands or contracts.

Figure 8:
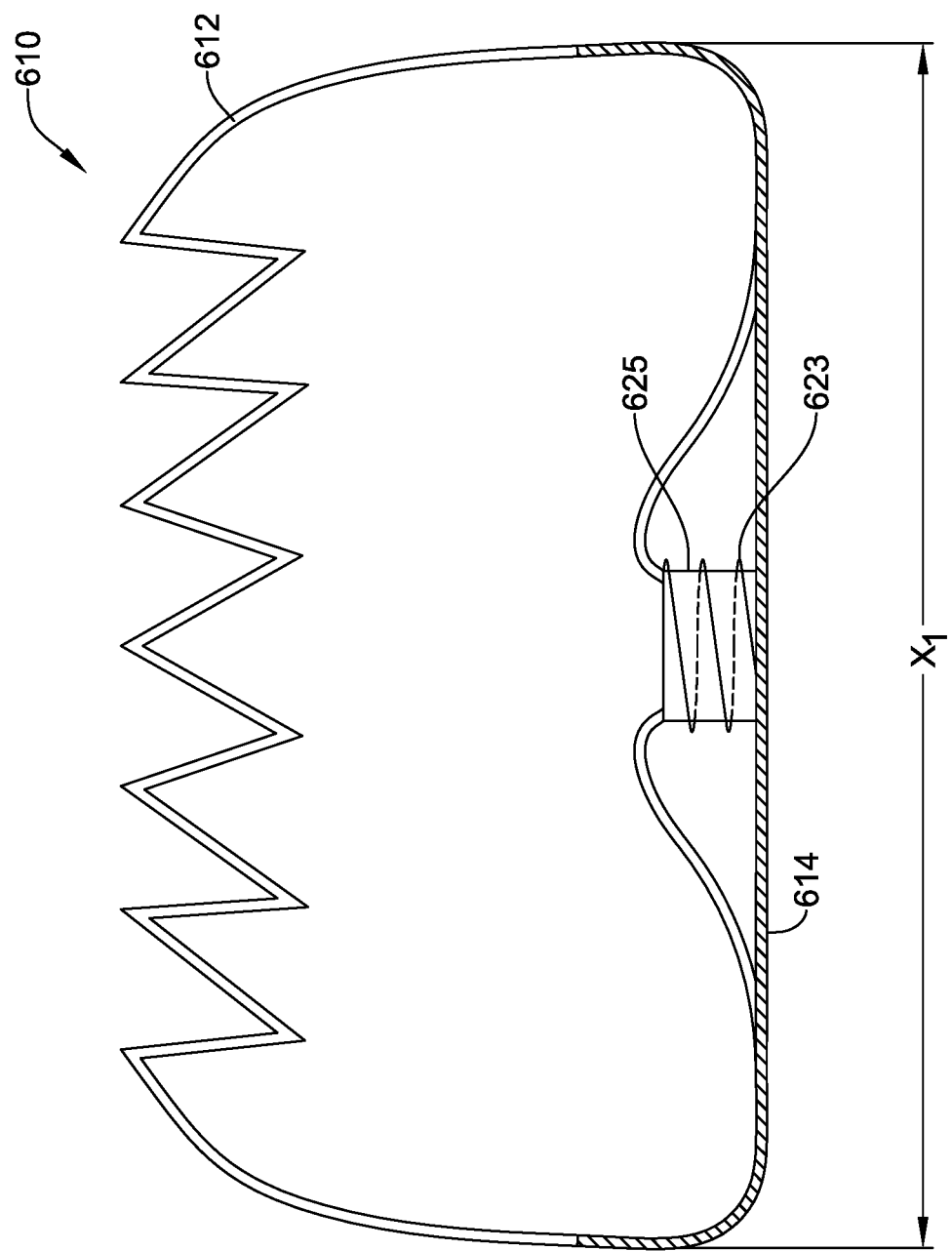
FIG. 8 is a plan view of another example occlusive implant.
Figure 9:
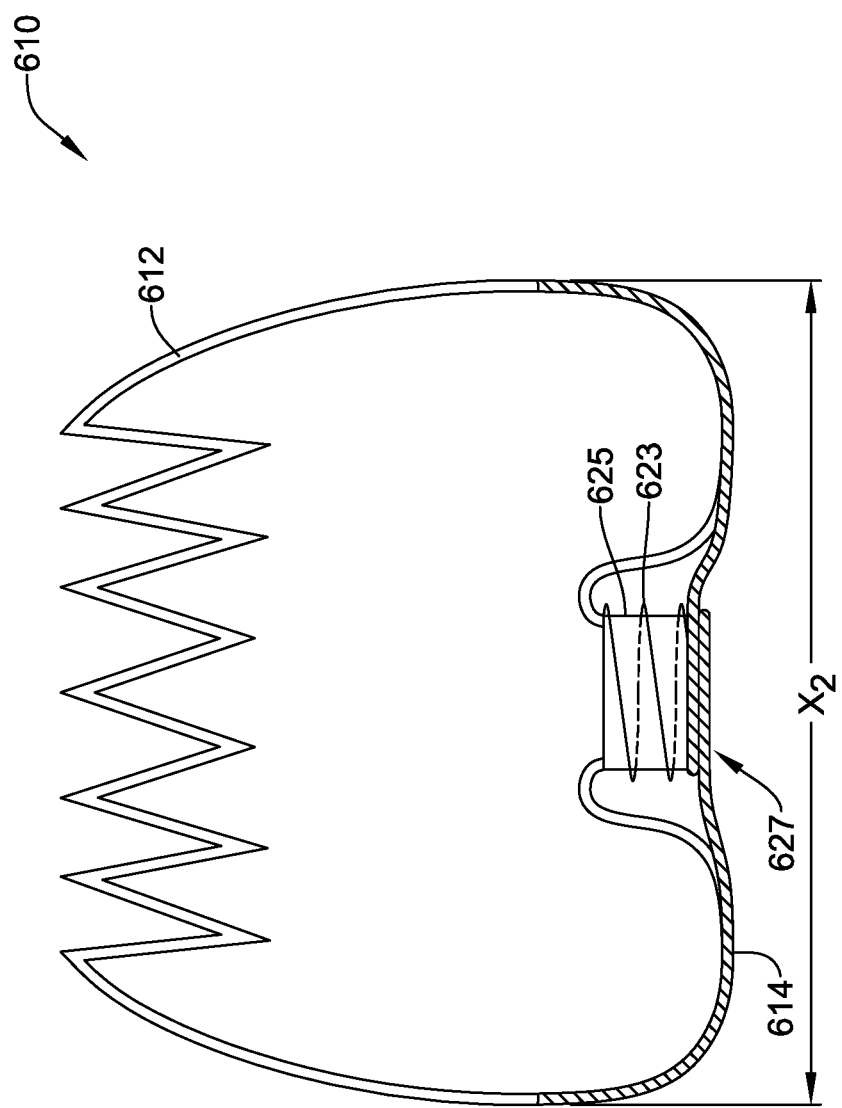
FIG. 9 is a plan view of another example occlusive implant.

FIGS. 8-9 illustrate another medical device 610, which may be similar in form and function to the other medical devices discussed above. In the interest of simplicity, FIGS. 8-9 illustrate a "silhouette" of the occlusive implant 610 in an expanded configuration. The medical device 610 may include an expandable framework 612. The expandable framework 612 may be configured to shift between an unexpanded configuration and an expanded configuration. Additionally, and similar to medical device 10 described above, the medical device 610 may include an occlusive member 614 disposed along the exterior surface of the expandable framework 612.

Further, FIG. 8 illustrates that the expandable framework 612 may include a first diameter depicted as dimension "$X_1$" in FIG. 8. As will be illustrated in FIG. 9, the expandable framework 612 may be shift from an expanded configuration (shown in FIG. 8) to an unexpanded configuration (shown in FIG. 9). The diameter of the expandable framework 612 shown in FIG. 9 is depicted as dimension "$X_2$", whereby the diameter $X_2$ may be less than the diameter $X_1$.

It can be appreciated from FIGS. 8-9 that as the expandable framework 612 contracts from an expanded diameter (shown in FIG. 8) to a contracted diameter (shown in FIG. 9), the occlusive member 614 may loosen. In other words, the occlusive member 614 may sag away from the outer surface of the expandable framework 612 as the expandable framework 612 contracts from an expanded diameter to a contracted diameter. Therefore, in some instances it may be desirable to design the medical device 610 to include one or more elements which tighten the occlusive member 614 around the outer surface of the expandable framework 612.

To that end, FIG. 8 and FIG. 9 illustrate that the medical device 610 may include a spring (e.g., coil, etc.) member 623 disposed adjacent to the hub member 625. The spring member may include a first end which is coupled to the hub member 625 and a second end which is coupled to the occlusive member 614. It can be appreciated that as the expandable framework 612 contracts from an expanded diameter to a contracted diameter, the spring member may "wind" and tighten the occlusive member 614. The winding of the occlusive member 614 is illustrated by the reference number 627 in FIG. 9.

It can be appreciated that the spring member 623 may be designed to wind the occlusive member 614 around the hub member 625 to collect the slack of the occlusive member 614 and thereby maintain the occlusive member 614 under tension (e.g., substantially taut) along the outer surface of the expandable framework 612. Keeping the occlusive member 614 taut along the outer surface of the expandable framework 612 may prevent the occlusive member 614 from forming wrinkles therein as the expandable framework 612 shifts between an unexpanded configuration and an expanded configuration. It may be desirable to reduce wrinkles in the occlusive member 614 to reduce the likelihood that particulate (e.g., thrombus) may be trapped therein.

Figure 10:
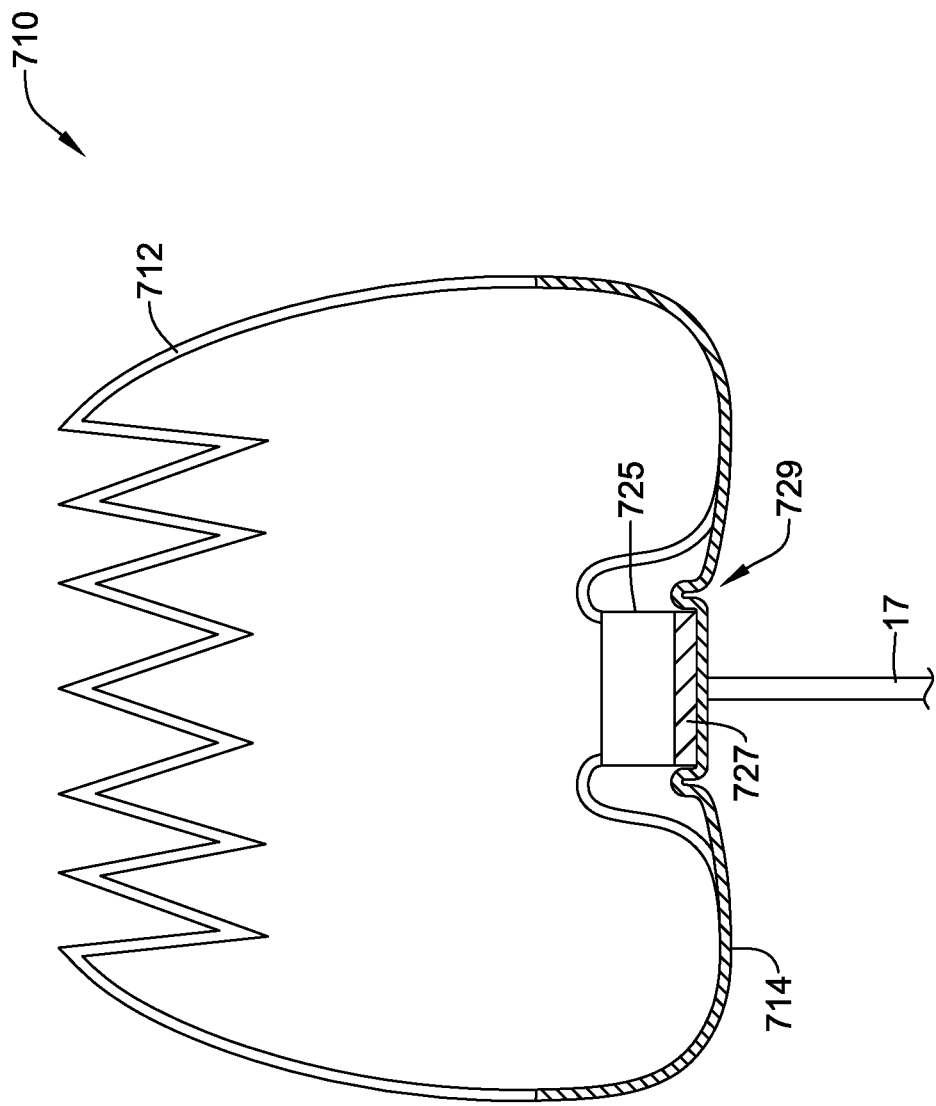
FIG. 10 is a plan view of another example occlusive implant.
Figure 11:
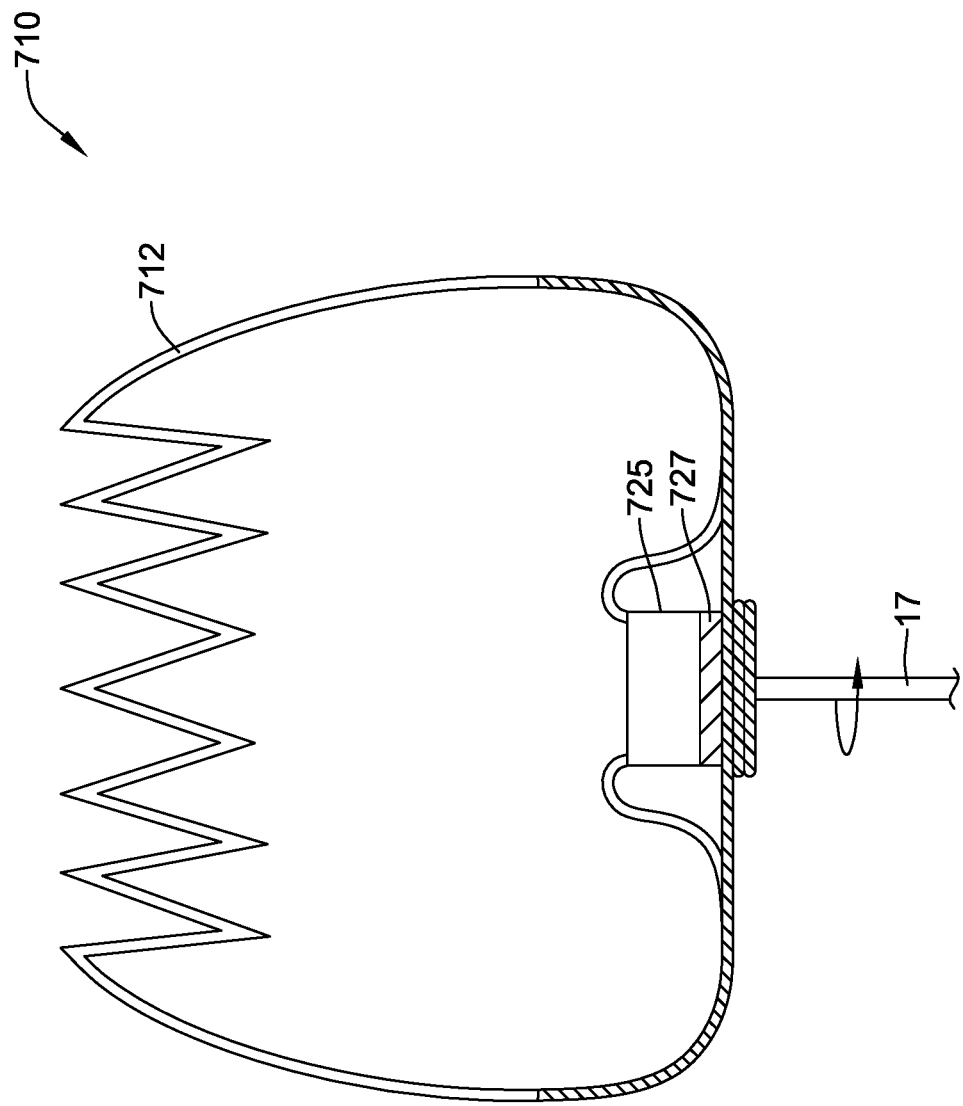
FIG. 11 is a plan view of another example occlusive implant.
Figure 12:
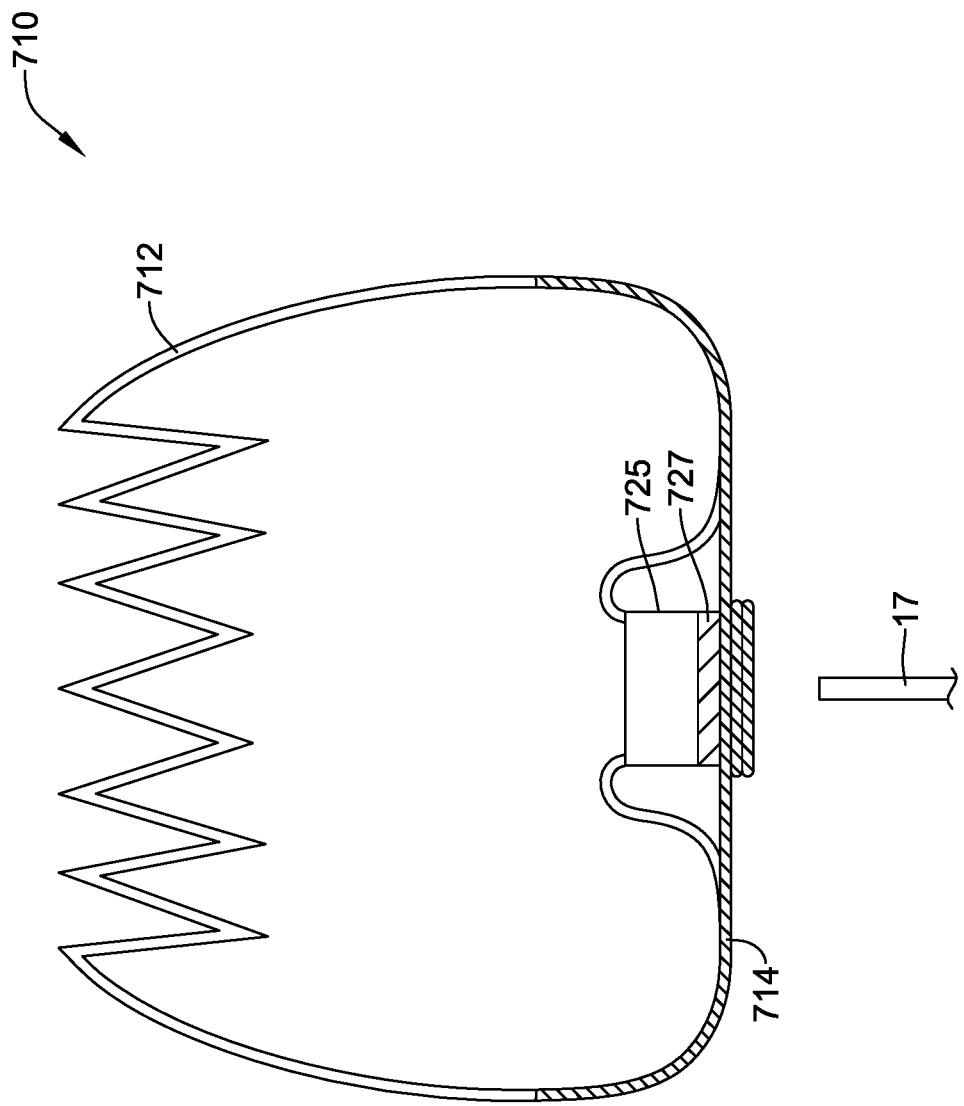
FIG. 12 is a plan view of another example occlusive implant.

FIGS. 10-12 illustrate another medical device 710, which may be similar in form and function to the other medical devices discussed above. In the interest of simplicity, FIGS. 10-12 illustrate a "silhouette" of the occlusive implant 710 in an expanded configuration. The medical device 710 may include an expandable framework 712. The expandable framework 712 may be configured to shift between an unexpanded configuration and an expanded configuration. Additionally, and similar to medical device 10 described above, the medical device 710 may include an occlusive member 714 disposed along the exterior surface of the expandable framework 712.

Similar to the medical device 610 described above, in some instances it may be desirable to design medical device 710 include one or more elements which collect and tighten the occlusive member 714 around the outer surface of the expandable framework 712 as the expandable framework 712 contracts from an expanded configuration to an unexpanded configuration. To that end, the medical device 710 may include a ratcheting member 727 coupled to a hub member 725, the occlusive member 714 or both the hub member 725 and the occlusive member 714. Additionally, the ratcheting member 727 may be coupled to the core wire 17 (described above with respect to FIG. 1). FIG. 10 illustrates the occlusive member 714 including bunched occlusive member material 729 positioned adjacent to the hub member 725.

FIG. 11 illustrates that the core wire 17 may be rotated, which, in turn, rotates the ratcheting member 727. Further, the rotation of the ratcheting member 727 may wind and tighten the loose occlusive material, thereby maintaining the occlusive member 714 under tension (e.g., substantially taut) along the outer surface of the expandable framework 712. It can be appreciated that rotation of the occlusive member 714 (via rotation of the core wire 17 and the ratcheting member 727), may spirally cinch the occlusive member 714 tight around the hub member 725. It can be appreciated that the ratcheting member may be designed to permit rotation in a first direction, while resisting rotation in a second direction opposite to the first direction.

FIG. 12 illustrates that, in some examples, it may be desirable to remove the core wire 17 from the medical device 710. For example, the medical device 710 may be designed such that clockwise rotation of the core wire 17 winds and tightens the occlusive member 714, while counterclockwise rotation of the core wire 17 may release (e.g., unscrew) the core wire 17 from the medical device 710. It can be further appreciated that the ratcheting member 727 may prevent the occlusive member 714 from unwinding as the core wire is removed from the medical device 710. It is noted that FIGS. 11-12 illustrate the occlusive member 714 pulled taut along the expandable framework 712.

Figure 13:
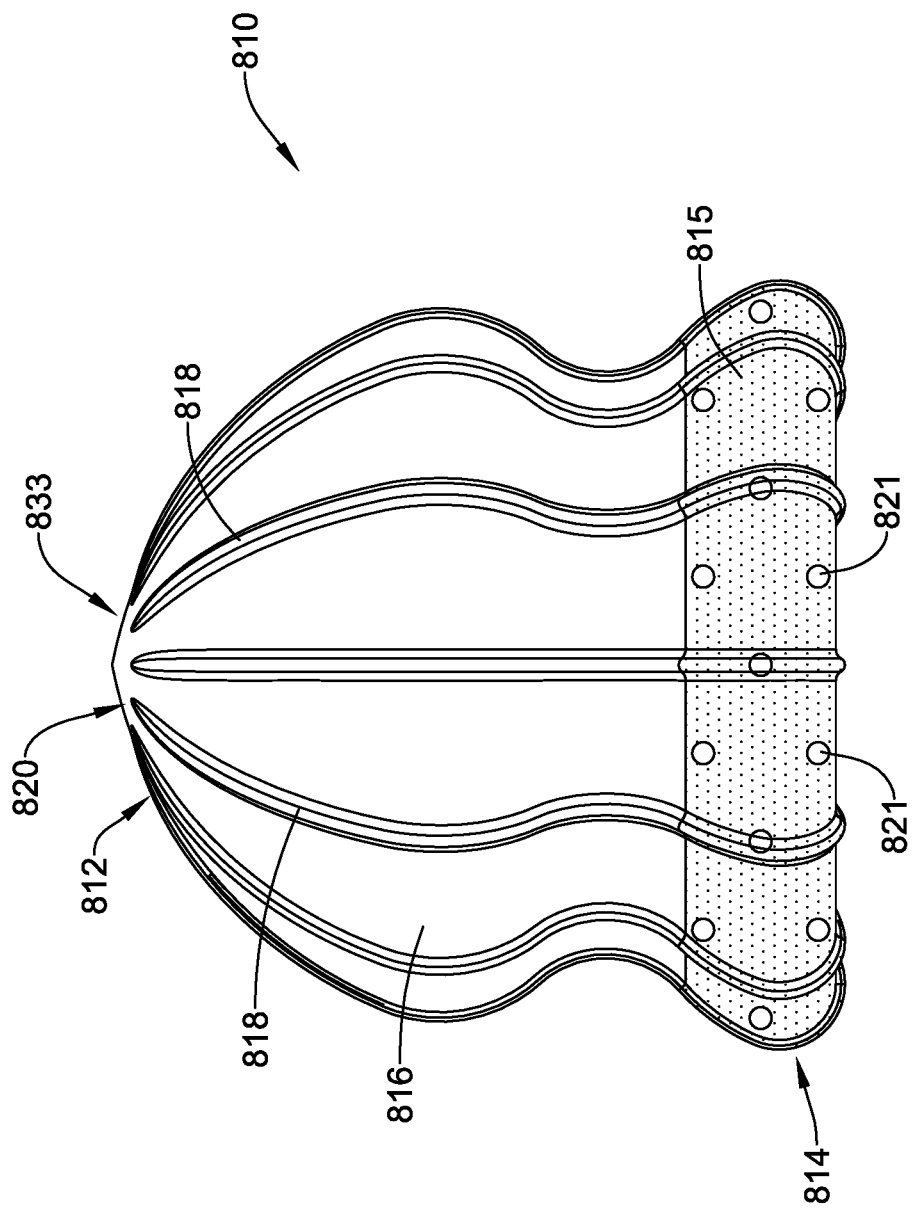
FIG. 13 illustrates another example occlusive implant.

FIG. 13 illustrates another example medical device 810. The medical device 810 may include a first end region 812 and a second end region 814. As will be discussed in greater detail below, the first end region 812 may include the portion of the medical device 810 which extends farthest into a left atrial appendage, while the second end region may include the portion of the medical device 810 which is positioned closer to an opening of the left atrial appendage.

The medical device 810 may include an expandable member 816. The expandable member 816 may also be referred to as an expandable balloon 816. The expandable member 816 may be formed from a highly compliant material (e.g., "inflation material") which permits the expandable member 816 to expand from a first unexpanded (e.g., deflated, collapsed) configuration to a second expanded (e.g., inflated) configuration. In some examples, the expandable member 816 may be inflated to pressures from about 4 psi to 200 psi. It can be appreciated that the outer diameter of the occlusive member 810 may be larger in the expanded configuration versus the unexpanded configuration.

In some examples, the expandable member 816 may be constructed from silicone or a low-durometer polymer, however, other materials are contemplated. Additionally, the expandable member 816 may be impermeable to blood and/or other fluids, such as water. In some embodiments, the expandable member 816 may include a woven, braided and/or knitted material, a fiber, a sheet-like material, a metallic or polymeric mesh, or other suitable construction. Further, in some embodiments, the expandable member 816 may prevent thrombi (e.g., blood clots, etc.) originating in the left atrial appendage from passing through the occlusive member 810 and into the blood stream. Further, in some instances the occlusive member 810 may promote endothelial growth after implantation, thereby effectively removing the left atrial appendage from the patient's circulatory system. Some suitable, but non-limiting, examples of materials for the occlusive member 810 are discussed below.

FIG. 13 further illustrates that occlusive member 810 may include one or more spine members 818 extending along the longitudinal axis 50 of the expandable member 816 from the second end region 814 to the first end region 812. In some examples disclosed herein, the spine members 818 may be described as positioning members 818. Each of the spine members 818 may include a first end 820 and a second end (not shown in FIG. 13). FIG. 13 further illustrates that the each of the individual spine members 818 may be spaced apart from adjacent spine members 818. In other words, the spacing between adjacent spine members 818 may be substantially uniform around the circumference of the expandable member 816. In some examples, the spine members 818 may include one or more materials which are stiffer, higher durometer materials than the material for which the expandable member 816 is constructed. Some suitable, but non-limiting, examples of materials for the spine members 818 are discussed below.

However, it is contemplated that in some instances the spacing between spine members 818 may not be uniform. In some examples, the spacing between adjacent spine members 818 may be variable (e.g., non-uniformly spaced) around the circumference of the expandable member 816. Additionally, it is contemplated that the spine members 818 may form a framework in which the spine members 818 are connected to one another via a series of laterally extending members. A variety of different geometries for example frameworks are contemplated.

As illustrated in FIG. 13, the first end region 812 of the expandable member 816 may extend radially inward to form an apex region 833. Additionally, as shown in FIG. 13, each of the first end portions 820 of each of the spine members 818 may extend radially inward toward the apex region 833 of the expandable member 816. Additionally, the medical device 810 may include an occlusive member 814 disposed along the exterior surface of the expandable member 816.

In some instances, it may be beneficial to design the medical device 810 to include one or more apertures 821 disposed along the occlusive member 814. Similar to that described above with respect to the occlusive member 14, the occlusive member 814 may include a mesh structure 815 disposed along the exterior surface of the expandable member 816. For example, the mesh structure 815 may include elastic fibers woven together to form the mesh structure 815. In some examples, the mesh structure 815 may include inelastic fibers interwoven with elastic fibers.

As discussed above, it may be beneficial to include one or more apertures 821 disposed with the mesh structure 815. Each of the apertures 821 may be formed from a rigid material (e.g., polymeric rings), wherein the apertures 821 resist deformation as the occlusive member 814 expands or contracts with the expansion or contraction of the expandable member 816. In some examples, the diameter of each of the apertures 821 may be about 10 µm to 200 µm, or about 15 µm to 150 µm, or about 25 µm. However, this is not intended to be limiting. Further, it is contemplated that the apertures 821 may be formed from an elastic and/or semi-elastic material.

In some examples it may be desirable to design the apertures 821 to allow blood to flow therethrough. It can further be appreciated that designing the occlusive member 814 to include a plurality of apertures 821 formed from a rigid material may result in the occlusive member 814 maintaining a consistent "porosity" as the occlusive member 814 expands or contracts with the expansion or contraction of the expandable member 816. Maintaining a consistent porosity as the occlusive member 814 expands or contracts may be desirable to maintain a consistent filtering capacity for a given amount of blood flowing through the occlusive member 814 independent of the degree to which the expandable member 816 expands or contracts. The consistent porosity may also provide sufficient occlusive material to optimize endothelial growth thereon.

Figure 14:
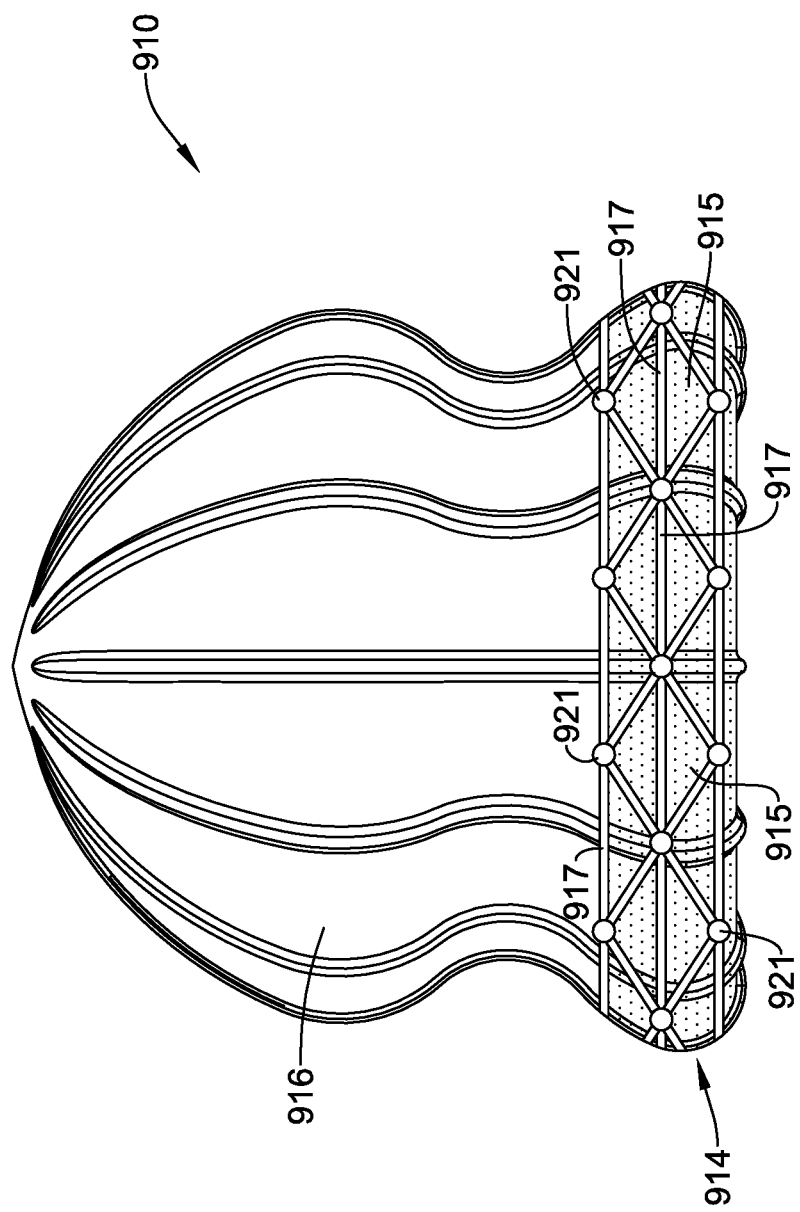
FIG. 14 illustrates another example occlusive implant in an expanded configuration.

FIG. 14 illustrates another example medical device 910. The medical device 910 may be similar in form and function as the medical device 910 described above. For example, the medical device 910 may include an expandable member 916. The expandable member 916 may be configured to shift between an unexpanded configuration and an expanded configuration. Similar to medical device 10 described above, the medical device 910 may include an occlusive member 914 disposed along the exterior surface of the expandable member 916.

Additionally, FIG. 14 illustrates that in some examples, it may be beneficial to design the occlusive member 914 to include a plurality of fiber elements 917 interconnected with one another to form a fiber frame and/or matrix. Further, in some examples, the fiber matrix may include an aperture 921 positioned at the ends of one or more fiber elements 917. In other words, the apertures 921 may act as a connection (e.g., termination) point for one or more of the fiber elements 917. Additionally, the fiber matrix (including the fiber elements 917 and the apertures 921) may be engaged with one or more mesh portions 915. For example, in some instances, the fiber matrix may be integrated with the mesh structure. In some examples, the fiber matrix (including the fiber elements 917 and the apertures 921) may include interstices within which the mesh portions 915 are positioned. The mesh portions 915 may be formed from an elastic or inelastic material. In some examples, a combination of inelastic and elastic mesh portions may interspersed within the fiber matrix (including the fiber elements 917 and the apertures 921). In some examples, the fiber matrix (including the fiber elements 917 and the apertures 921) may include an auxetic structure.

Similar to the apertures described with respect to FIG. 7, the apertures 921 may result in the occlusive member 914 maintaining a consistent porosity as the occlusive member 914 expands or contracts with the expansion or contraction of the expandable member 916. Maintaining a consistent porosity as the occlusive member 914 expands or contracts may be desirable to maintain a consistent filtering capacity for a given amount of blood flowing through the occlusive member 914 independent of the degree to which the expandable member 916 expands or contracts. The consistent porosity may also provide sufficient occlusive material to optimize endothelial growth thereon.

It can be appreciated that the fiber matrix (including the fiber elements 917 and the apertures 921) in combination with the woven mesh portions 915 may be compressed or stretched. It can be further appreciated that the fiber matrix (including the fiber elements 917 and the apertures 921) in combination with the woven mesh portions 915 may be designed such that they keep the occlusive member 914 taut against the outer surface of the expandable member 916. Further, it can be appreciated that the ability of the fiber matrix (including the fiber elements 917 and the apertures 921) in combination with the woven mesh portions 915 to expand and/or contract while maintaining a tension along the occlusive member 914 may keep the occlusive member 914 taut against the outer surface of the expandable member 916 as the size of the expandable member 912 changes (e.g., via expansion or contraction).

Figure 15:
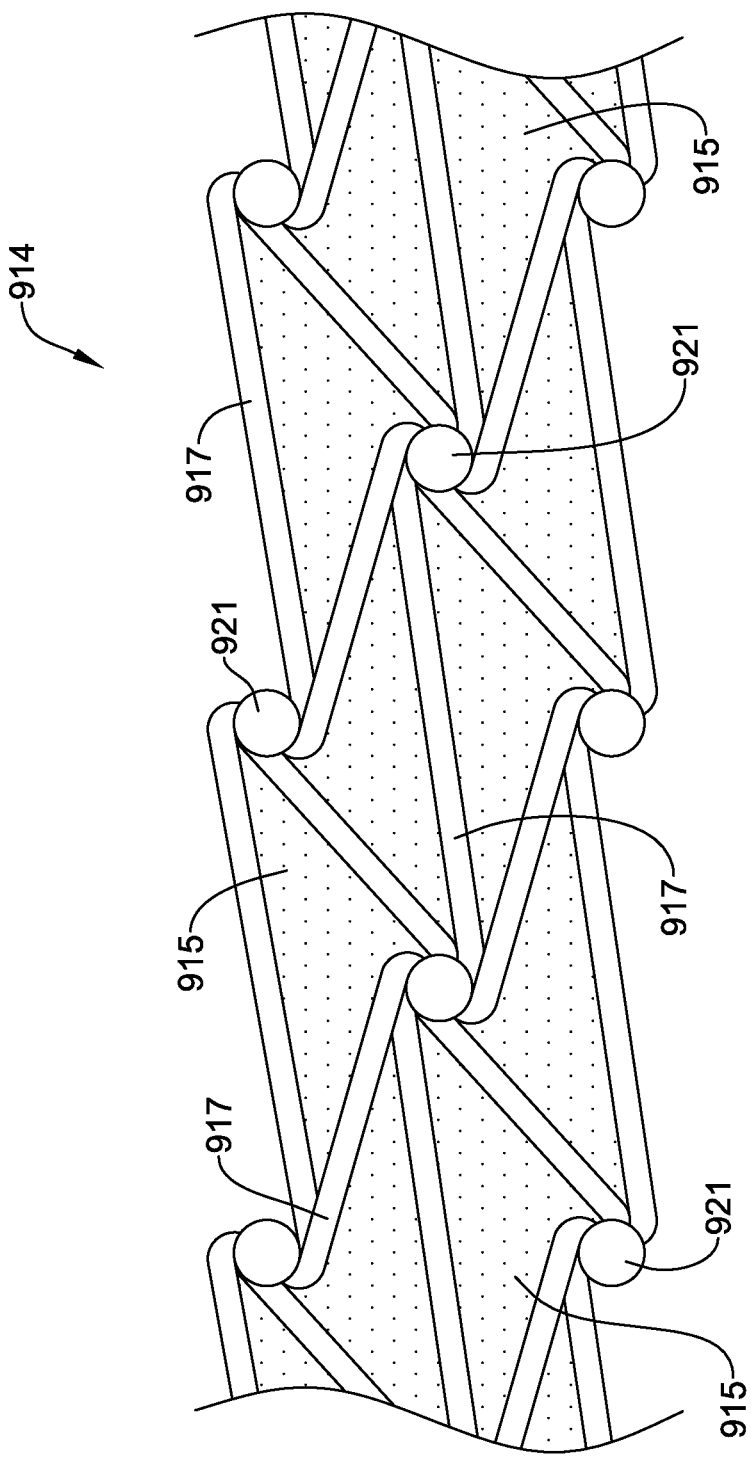
FIG. 15 illustrates a portion of the occlusive member illustrated in FIG. 14 in an unexpanded configuration.

FIG. 15 illustrates a detailed view of the occlusive member 914 (described above) in a relaxed (e.g., unexpanded) configuration. As illustrated in FIG. 15, the fiber elements 917 may rotate and/or wrap around the apertures 921 as the fiber matrix (including the fiber elements 917 and the apertures 921) shifts from an expanded to a collapsed configuration. In some examples, the fiber elements 917 may act as a framework for the mesh 915. Under tension, the fibers 917 may unwind from the circumference of the apertures 921, in conjunction with the mesh 915, and may keep taught against implant frame 916. Additionally, the elastomeric properties may differ between the fiber elements 917 and the mesh 915, such that there is an acceptable equilibrium of tension applied to conform to member 916.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MRI) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. An occlusive implant, comprising:
   an expandable framework configured to shift between a first compact configuration and a second expanded configuration;
   an occlusive member disposed along at least a portion of an outer surface of the expandable framework;
   first and second resilient members coupled to the occlusive member,
   a hub member disposed adjacent to the occlusive member,
   wherein the first resilient member includes a coil member disposed around the hub member,
   wherein the coil member is adapted to tighten the occlusive member as the expandable framework shifts between the first compact configuration and the second expanded configuration,
   wherein the second resilient member includes a spring having a first end attached to the occlusive member and a second end coupled to the expandable framework;
   wherein the first and second resilient members are configured to keep the occlusive member taut against an outer surface of the expandable framework in both the first compact configuration and the second expanded configuration.

2. The occlusive implant of claim 1, further comprising a third resilient member including an elastic band, wherein the elastic band has a first end attached to the occlusive member and a second end coupled to the expandable framework.

3. The occlusive implant of claim 1, further comprising one or more elastic fibers integrated with the occlusive member, and wherein the one or more elastic fibers are designed to elongate and contract as the expandable framework shifts between the first compact configuration and the second expanded configuration.

4. The occlusive member of claim 3, wherein the occlusive member includes one or more inelastic fibers and wherein the one or more elastic fibers are interwoven with the one or more inelastic fibers.

5. The occlusive member of claim 3, further comprising a plurality of rigid members disposed along the occlusive member, wherein each of the plurality of rigid members includes an aperture designed to permit fluid to flow therethrough.

6. The occlusive member of claim 1, wherein the occlusive member includes a mesh structure, further comprising one or more elastic members interconnected to form an elastic matrix, and wherein the mesh structure is coupled to the elastic matrix.

7. The occlusive member of claim 6, wherein the elastic matrix includes a plurality of interstices spaced throughout the elastic matrix, and wherein the mesh structure is disposed within the plurality of interstices.

8. The occlusive implant of claim 1, wherein the spring includes a coiled portion.

9. The occlusive implant of claim 1, wherein the spring includes a helical portion.

10. The occlusive implant of claim 1, wherein the spring includes a twisted portion.

11. The occlusive implant of claim 1, wherein the spring includes a twisted portion.

12. The occlusive implant of claim 1, wherein the spring includes a zig-zag portion.

13. An occlusive implant, comprising:
    an expandable framework configured to shift between a first configuration and a second expanded configuration;
    an occlusive member disposed along at least a portion of an outer surface of the expandable framework;
    a hub member coupled to the expandable framework; and
    a tightening member coupled to the expandable framework, the occlusive member, or both the expandable framework and the occlusive member, the tightening member including a coil member disposed along the hub member and a spring coupled to the expandable framework and the occlusive member;
    wherein when rotated relative to the expandable framework, the coil member is configured to keep the occlusive member taut against an outer surface of the expandable framework in both the first configuration and the second expanded configuration.

14. The occlusive implant of claim 13, wherein the coil member is wound around an outer surface of the hub member, wherein a first end of the coil member is coupled to the hub member and a second end of the coil member is coupled to the occlusive member.

15. The occlusive implant of claim 13, wherein the spring includes a helical portion.

16. A method for occluding a left atrial appendage, the method comprising:
    advancing an occlusive implant to the left atrial appendage, the occlusive implant including:
       an expandable framework configured to shift between a first compact configuration and a second expanded configuration;
       an occlusive member disposed along at least a portion of an outer surface of the expandable framework;
       a hub member disposed adjacent to the occlusive member;
       first and second resilient members coupled to the occlusive member, wherein the first resilient member includes a coil member disposed around the hub member, wherein the second resilient member includes a spring having a first end attached to the occlusive member and a second end coupled to the expandable framework;
    expanding the expandable framework within the left atrial appendage, wherein during expanding the expandable framework within the left atrial appendage the first and second resilient members keep the occlusive member taut against an outer surface of the expandable framework.

* * * * *